United States Patent [19]
Gill et al.

[11] Patent Number: 4,899,729
[45] Date of Patent: Feb. 13, 1990

[54] EXPANSIBLE CANNULA

[76] Inventors: Steven S. Gill, 25 New Close, Knebworth, Hertfordshire; Joseph F. Jackson, 1 West Royd Villas, Halifax, West Yorkshire, HX1 3L5, both of England

[21] Appl. No.: 204,165

[22] Filed: Aug. 3, 1988

Related U.S. Application Data

[63] Continuation of Ser. No. 868,788, May 29, 1986, abandoned.

[30] Foreign Application Priority Data

May 30, 1986 [GB] United Kingdom ............... 8513702

[51] Int. Cl.$^4$ .................... A61B 1/32; A61M 29/00
[52] U.S. Cl. ........................................ 128/3; 606/198
[58] Field of Search ................. 128/343, 341, 200.26, 128/345, 753, 754, 3; 604/107, 108, 104

[56] References Cited

U.S. PATENT DOCUMENTS

| | | | |
|---|---|---|---|
| 668,879 | 2/1901 | Miller | 128/345 X |
| 3,044,461 | 7/1962 | Murdock | 128/17 |
| 3,788,318 | 1/1974 | Kim et al. | 128/343 X |
| 3,789,852 | 2/1974 | Kim et al. | 604/104 |
| 4,211,234 | 7/1980 | Fisher | 128/343 X |
| 4,451,256 | 5/1984 | Weikl et al. | 128/343 X |
| 4,513,754 | 4/1985 | Lee | 128/753 |
| 4,716,901 | 1/1988 | Jackson et al. | 128/343 |

FOREIGN PATENT DOCUMENTS 2515756  9/1976  Fed. Rep. of Germany .......... 128/3

*Primary Examiner*—Michael H. Thaler
*Attorney, Agent, or Firm*—Richard E. Jenkins

[57] ABSTRACT

The invention relates to a surgical cannula for introducing instruments, scopes or tubing into body cavities or organs. The cannula comprises a conical tubular stem which is formed of thin sheet material, such as beryllium copper, the sheet material being coiled or partially coiled so that if is capable of opening up from a closed condition by reducing the cone angle, thereby increasing the diameter of the stem at the distal end.

In the preferred arrangement, the proximal end of the stem is clamped between two tubular elements fitted one inside the other.

The invention also includes the combination of the expansible cannula and a guide rod adapted to pass through the stem and bored throughout its length to receive a guide wire. The guide rod may have a slightly enlarged distal end and the arrangement be such that passage of the enlarged distal end through the distal end of the stem causes a slight opening out of the distal end to allow passage of the enlargement.

When a blunt instrument such as a nephroscope is forced through the bore of the stem from the relatively large proximal end, the stem will expand by uncoiling until the stem provides a substantially parallel-sided bore through which the blunt instrument can pass.

According to a second aspect of the invention an expansible cannular has a stem formed by a plurality of thin sheet material leaves each of arcuate cross-section and overlapped so that together they form a tube which can be increased in diameter by reducing the overlap between the leaves.

11 Claims, 5 Drawing Sheets

EXPANSIBLE CANNULA

This is a continuation of application Ser. No. 868,788, filed May 29, 1986, now abandoned.

The present invention relates to a surgical appliance and method of introducing instruments, scopes or tubing into body cavities or organs. The invention is applicable to the treatment of humans and will be so described hereinafter, but it should be understood that with appropriate modifications, it could also be applied in veterinary practice. Whilst the apparatus can be used in a variety of surgical operations, one particularly use is for accurate placing instruments, scopes or tubin deep within the body cavities or organs, for example under X-ray guidance. It also has significant advantages over curently available apparatus for introducing such devices into soft and hightly vascular organs such as the liver or kidney. One form of the invention is also useful in forming and sustaining an adequately sized hole in tissue for brain surgery.

An increasing number of therapeutic and investigative procedures which at one time were impossible due to inaccessibility or required major surgery, are now being performed percutaneously via scopes, and various specially designed instruments are introduced under X-ray guidance. These procedures may be carried out under local anaesthesia and, after dilating up a passage through the tissues, these devices may be passed accurately to the target lesion. Some examples of such procedures include:

(1) The passage of scopes for observation and diagnosis. (2) Taking biopsies or removing diseased tissue via or under X-ray guidance.

(3) The accurate implanation of protheses into organs.

(4) The accurage implantation of radioisotopes for the treatment of localised carcinoma.

(5) The placement of drains into collections of fluid or pus in the abdominal or thoracic cavities.

(6) The placement of catheters into the biliary or urogenital system for drainage.

(7) The removal of foreign bodies or stones from organs.

Apart from the obvious advantage of avoiding the immobility associated with major surgery, patients who are unfit for such surgery may now be helped by the techniques described above. It is also of note that these methods are extremely cost effective as they save enormous expense of surgery and prolonged after care.

The problem which this invention is concerned with is in the creation and sustaining of a passage through the tissues, and along which scopes, instruments or tubes may be passed to the target lesion for these therapeutic or investigative procedures to be performed.

Taking as an example the insertion of a nephroscope into the urine collecting system of the kidney (the renal pelvis) for the extraction of a stone; the currently used method is to pass a fine needle through the skin of the patient's loin, and, under X-ray guidance, to direct it through the kidney substance and into the renal pelvis (the depth of penetration being usually about 10 to 15 centimeters). To ensure that the needle has reached the correct position, radio opaque dye may be injected down the needle and its dispersal into the renal pelvis viewed. A guide wire (approximately 0.75 millimeters diameter) is then passed through the bore of the needle and the needle withdrawn, leaving the guide wire alone in situ. As the diameter of the nephroscope to be passed may be as much as 9 millimeters, a passage must then be dilated around the guide wire to accept it. Conventionally this is done by passing a dilator, which is a blunt-ended rod with a hole down its axis, of 2 to 3 millimeters diameter down the guide wire to the target site, then withdrawing it and repeating the procedure with a larger diameter dilator, and so on, until the required passage is created. Alternatively, the passage may be created by passing a small diameter dilator down the guide wire, then, leaving this in situ and after a period to allow some recovery of the damaged tissue passing a closely fitting larger diameter tube over the guide wire to further dilate the tissues. Following that successively larger diameter tubes are passed over the preceding ones, until the desired degree of dilation has been achieved. Once the passage of required size has been created, the nephroscope is then passed into the renal pelvis and the kidney stone extracted through the bore of the scope. In some cases, a large stone may require crushing prior to extraction and this can be performed by instruments also passed down the scope.

There are a number of inherent problems with these currently used methods of dilating up a channel through the tissues. When the operator advances the types of dilator described above, the force exerted is of course in the direction of the axis of the dilator. However, the surgeon hopes to achieve displacement of the tissues in a direction substantially at right angles to the applied force, that is radially outwards from the axis of the dilator. The degree to which the applied force in converted to act in the desired direction depends on the size and shape of the dilator, a sharply pointed and gradually tapered dilator being the most efficient. The rod type dilators described above are blunt nosed for safety in order to avoid severing blood vessels. To ensure a uniform degree of dilation over the greater proportion of their inserted length, the rod type dilators expand rapidly from the tip of a fixed diameter. The greater proportion of the applied force thus acts to compress and thereby damage the tissues ahead of the dilator, or alternatively displace the organ away from the dilator as one attempts to insert it.

For tissue to be displaced radially outwards from the axis of the advancing dilator without damaging it, the tissue must be able to stretch over the blunt tip of the dilator and in so doing, must be capable of withstanding the considerable sheering forces imposed upon it. In the case of the kidney, and for that matter the liver, the tissue has little resilience and although it can be compressed to some extent, it will withstand little if any stretch and is easily disrupted by sheering forces. The result of passing a rod type dilator into this friable tissue is that the dilator first compresses the tissues ahead of itself and then, because the tissue is incapable of stretching over the blunt nose of the dilator, the tissue is pulverised by the sheering and compressive forces exerted. A hole is thus created in the organ by tissue destruction and the pulverised core is compressed at the distal end of the dilator or squeezed around its circumference.

When dilating up a passage through the kidney substance and into the renal pelvis for stone extraction, an additional problem is that the pulverised renal tissue is pushed into the renal pelvis. This debris and blood clots may obstruct the flow of urine from the renal pelvis into the ureter; it is therefore necessary, using the currently available techniques, to leave a drainage tube in the kidney after stone extraction. This "nephrostomy tube"

is left in situ for 3 to 4 days after the operation, and acts as a safety valve allowing urine to escape from the renal pelvis prior to clearance of the obstruction.

As is apparent from the above description, the kidney undergoes a considerable amount of trauma during the procedure. Not only is a portion of it destroyed, but the tissue around the hole creates swelling in reaction to the injury and raw edges of the damaged tissues bleed profusely. Blood loss can be considerable, and has been the cause of several fatalities.

In the method of tissue dilation whereby a dilator is introduced, then withdrawn and replaced with dilators of successively large diameter, further problems are encountered. Firstly, upon withdrawal of a dilator, the raw surface bleeds and the surrounding tissue swells, partly occluding the hole created. On insertion of the successively larger dilator the oedematous tissue is sheered off causing further trauma and disrupting any clots which may have formed. Thus, more vessels are damaged encouraging greater haemmorrhage. Secondly, as one dilator is withdrawn, leaving the guide wire alone in situ, the guide wire then lies in a wider passage and is apt to change its position. The subsequent dilation may thus be off centre, creating a larger volume of damage than is necessary.

Dilation with the system of interlocking tubes causes an equivalent degree of tissue destruction to the system of successively larger rod dilators, because as each tube is advanced over the preceding one, it shears off more tissue. The advantage with this system however is that the continual pressure between the dilator and the surrounding tissue reduces the amount of haemorrhage during dilation.

With the foregoing factors in mind, a primary object of the present invention is to provide a means for introducing tubes, scopes or other instruments into body cavities or organs percutaneously, which avoids the drawbacks and difficulties referred to above.

In brain surgery, it is required to form and sustain a relatively large hole in the tissue (e.g. 25 millimeters in diameter) to permit the required investigation and surgical techniques. A problem which has in the main prevented the use of expansible devices for dilating up the tissue is that it is vital to reduce damage to the tissue.

According to a first aspect of the invention an expansible cannula comprises a concial tubular stem formed of thin sheet material at least partially coiled on itself so that it is capable of opening up from a closed condition to reduce the cone angle, thereby increasing the diameter of the stem at the distal end. Preferably the stem is biased by the resilience of the material which it is made into the closed condition. It is further preferred that the stem is made in sheet metal which is heat-treated after coiling, to give it the required resilience. The stem may be made in beryllium copper.

According to another preferred feature, the proximal end of the stem is clamped by fitting two tubular elements one inside and one outside the proximal end of the coiled stem and securing the two tubular elements together. In the preferred arrangement, the tubular element which fits into the end of the stem has a collar engaging with the outer face of a flange on the end of the stem and the tubular element which fits over the stem engages with the opposite face of the flange, there being a nut engaging with the outer end of the collar, and having screw-threaded engagement with the tubular element which fits over the stem.

Preferably the bore of the stem, at its distal end, in the closed condition, is a close fit around a guide rod, bored thoughout its length, to pass over a wire extending through the skin of a patient to the site of the lesion. Such a guide rod serves to constrain the cannula to follow the path of the wire when the cannula is being used and it also provides support for the distal end of the coiled stem.

The invention also comprehends a guide rod adapted to pass through the bore of the stem at the distal end and bored throughout its length to receive a guide wire. The guide rod is preferably formed with a slightly enlarged distal end, and the arrangement of the stem may be such that passage of such an enlarged distal end through the distal end of the stem causes a slight opening out (uncoiling) of the distal end to allow passage of the enlargement, the distal end of the stem then contracting under its inherent resilience, on to the main portion of the guide rod behind the enlarged end, so that the enlarged end is located against the distal end of the stem. It will be appreciated that, with such a guide rod inserted into the stem, the cannula then comprises the stem and the guide rod. It is possible to introduce the cannula through the skin of a patient, and as the stem of the cannula follows the enlarged head of the guide rod, it gradually dilates the opening formed through the skin and any other tissue or organ through which the cannula is passed. In this mode of use, the combined cannula and guide rod function as a trocar.

Preferably the cone angle of the stem does not exceed 10° and in the preferred construction it is approximately 1.7°. With a small cone angle, the dilation of the skin or tissue on introduction of the trocar stem produces a minimum damage to the skin or tissue.

When a blunt instrument such as a nephroscope or expander tube is forced through the bore of the stem from the relatively large proximal end of the stem will expand by uncoiling, the uncoiling action being greatest at the distal end, until the stem provides a substantially parallel-sided bore through which the blunt instrument can pass. Again, the dilation of the skin and tissue which occurs due to this expansion of the stem is achieved with a minimum amount of damage to the skin and tissue, because the conical form of the stem provides an ideal means of converting the longitudinal motion of the blunt instrument into a radial expansion of the stem. Moreover, the dilation occurs smoothly and without any severe axial compression or shearing of the tissue.

According to a second aspect of the invention an expansible cannula comprises a stem formed by a plurality of thin sheet material leaves each of arcuate cross-section, each leaf being overlapped with the adjacent leaf or leaves so that, together, the leaves form a tube which can be increased in diameter by moving the leaves to reduce the overlap between them. Preferably each leaf has one longitudinal margin on the inside of an adjacent leaf and the other longitudinal margin on the outside of the or another adjacent leaf. In the preferred construction, there are three leaves each of which has one longitudinal edge inside the leaf on its anticlockwise side, and its other longitudinal leaf outside the leaf on the clockwise side.

Preferably the three leaves taper so that in the assembled condition they form a conical or frusto-conical stem, which tapers towards the distal end, so that when the stem is opened by exerting an expansion force to the inside of the stem, the distal ends of the leaves open to a greater extent than the proximal end (i.e. there is a greater reduction in the overlapping at the distal end than at the proximal end). This aspect of the invention may be combined with all the features of the first aspect of the invention.

The construction of three forms of cannula each in accordance with the first aspect of invention (the third form being also in accordance with the second aspect of the invention) and their method of use, will now be described by way of examples only, with reference to the accompanying drawings in which.

The principal element of the cannula shown in FIGS. 1 to 11, is a stem 10 (see FIGS. 4, 6 and 10) which is made by coiling a blank 12 (FIGS. 1 and 2) stamped from a thin sheet of beryllium copper. Beryllium copper is chosen, because it will not corrode, it is not significantly reactive to body acids, it is very ductile, and it responds to heat treatment at relatively low temperatures. The sheet material from which the blank 10 is formed is of the order of 50 microns (0.002 inches) thick, so that it has a leaf-like nature. The blank has a pair of tongues 18 and 20, and score lines 14 and 16 are formed in it, which divide the blank into a main, substantially trapezoidal portion 22, a triangular reinforcing portion 24 and the tongues 18 and 20. In addition, there are two parallel score lines 25 close to the longitudinal edge of the main portion 22.

It is desirable to reinforce part of the finished stem 10, and this is achieved by folding the blank on the score line 14 so that the triangular portion 24 lies against the underside of the main portion 22. A double fold is formed by folding over the margin of the main portion using the score lines 25. The folded blank may be rolled to press the folded over portions flat against the main portion. Also as a result of this folding, the two tabs 18 and 20 are brought face-to-face. The folding of the blank therefore produces a substantially triangular part of the blank which is of double the thickness of the remainder of the blank and will be referred to as the reinforced portion, in addition to which the longitudinal edge of the main portion 22 has a reinforcing seam.

Figure 1:
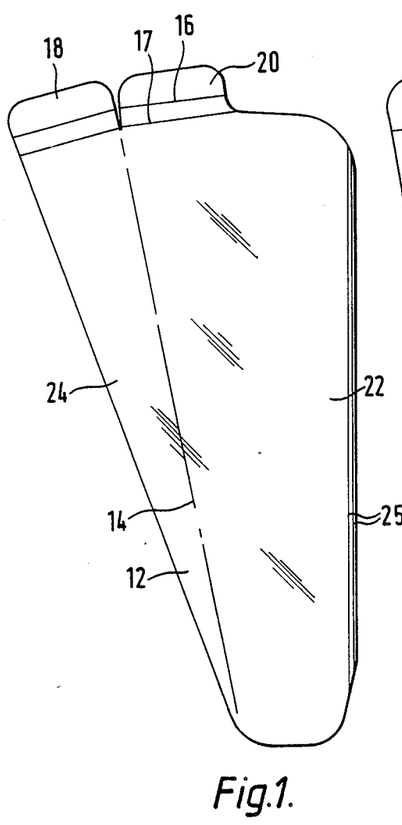
FIG. 1 shows a blank used in the manufacture of a cannula stem.
Figure 2:
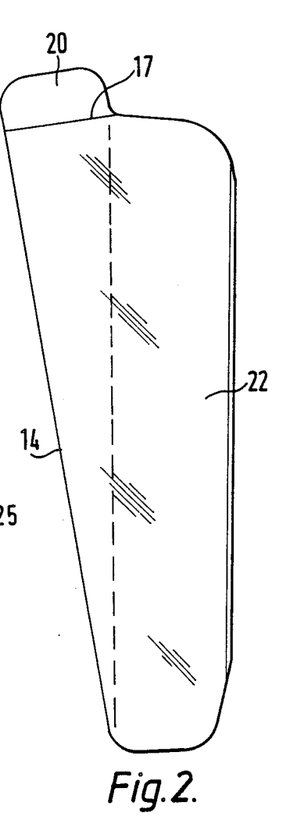
FIG. 2 shows the blank after a folding operation.

To form the tube-like stem 10, the blank 12 is then coiled on itself. Prior to coiling, the face-to-face tabs 18, 20 are folded over on the score line 16, onto the main portion 20. Then slits 28 (FIG. 3) are cut to a depth as indicated by a marker line 17 (FIGS. 1, 2).

Figure 3:
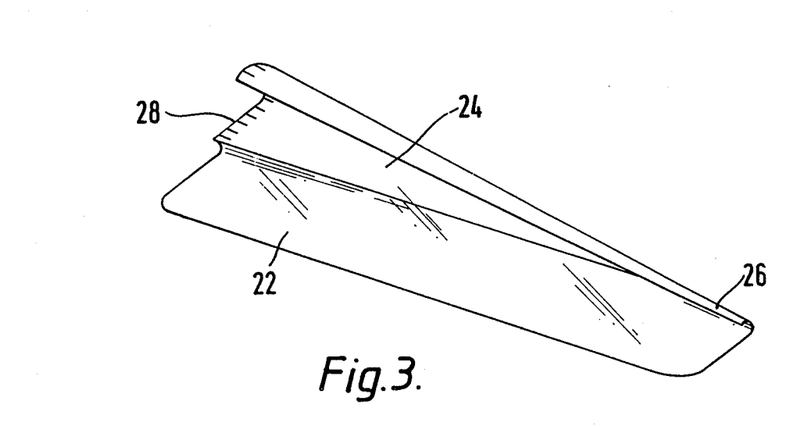
FIG. 3 shown an initial stage in a coiling operation.
Figures 4, 5A, 5B, 5C, 5D:
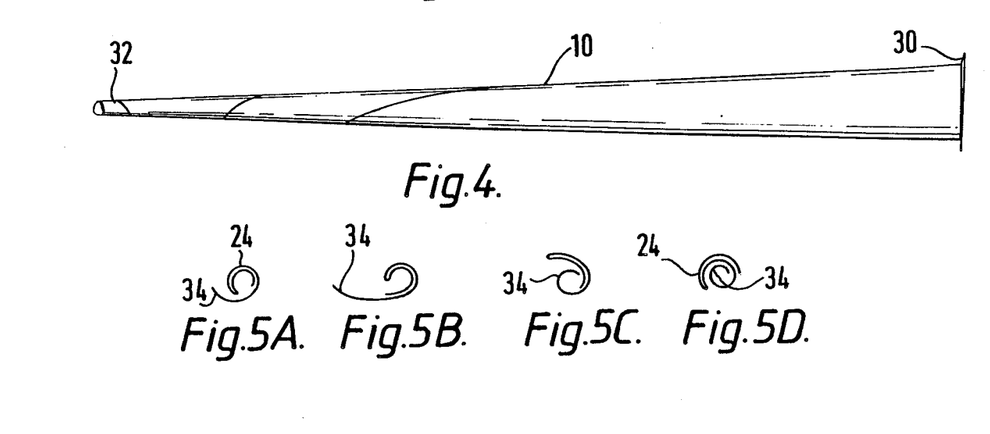
FIG. 4 shows a cannula stem formed by the coiling operation.
FIGS. 5A to 5D show cross-sections through the stem at various stages in a turning inside-out operation.

Coiling begins, as shown in FIG. 3, by turning over the reinforced triangular portion of the blank—see the turned over part 26. The coiling action is controlled so that the edge of the reinforced triangular portion (which at this stage will be on the inside) is maintained substantially straight. When the coiling is completed, this straight edge will then be parallel with the longitudinal axis of the stem. The folded over portion 24 is on the inside of the coil, and coiling is continued until the conical tubular stem 10 is formed—see FIG. 4. The outer edge—which is the seamed edge—follows a helical path with the helix angle increasing towards the proximal end of the stem. The series of short slits 28 allows the tabs 18,20 to be bent outwardly to form a flange 30 at the end of the coiling operation. It will be observed that the stem 10 has a small distal end 32, the bore of which is about 2.5 millimeters in diameter and that the cone angle is small, so that even at the proximal end, the bore of the stem is only about 10 millimeters diameter.

The stem 10 is then subjected to heat treatment, which may be at a temperature of approximately 300° C. to give the stem an appreciable resilience (spring effect). To avoid discolouring the stem the heat treatment may be carried out in a protective atmopshere. It is desirable that the finished stem should have a polished surface and to this end—and with a view to alleviating any toxic effect of the material from which the stem is made—the stem may be plated.

As a result of the coiling action, the reinforced triangular portion of the stem is on the inside. However, the coil is then turned inside-out to bring that reinforcing to the outside, the process for doing this being illustrated in FIG. 5. Starting at the distal end, the coil is first opened out, FIGS. 5A and 5B, then the seamed edge 34 is bent under the opened out reinforced edge—FIG. 5C—and the coil allowed to close using its spring effect, with the reinforced triangular portion on the outside—FIG. 5D. This action is transferred along the length of the stem towards the proximal end, until the entire stem is turned inside-out.

A short bush 38 (see FIGS. 6 and 7) is pushed into the proximal end of the stem, there being a collar 40 on the bush which engages with the flange 30—leaving a short projection of the bush beyond the flange 30. A rigid plastics tube 42 is a loose fit over the part of the stem which contains the bush 38, and at one end, this tube 42 has an external screw-thread 44. The screw-threaded end of the tube 42 engages with the opposite face of the flange 30 to the collar 40. The stem part of the trocar is completed by a retaining nut 46 which passes over the collar 40 and has a screw-threaded engagement with the tube 42. When the nut is tightened, it draws the tube 42 towards the collar 40, nipping the flange 30 and securing the flange axially on to the bush 38 and the tube 42. The stem only retains its closely coiled form due to its inherent resilience and there is sufficient radial clearance between the outside of the stem and the inside of the tube 42 to permit the inner convolution of the stem to turn about the longitudinal axis of the stem and to move axially, It should be mentioned, that the design of the blank and the coiling of the stem is such, that in the closed condition, the outer longitudinal edge of the reinforced portion of the stem extends in a substantially longitudinal straight line. However, the inner edge of the stem will have a helical and conical form. The cannula stem is then complete.

Figure 6:
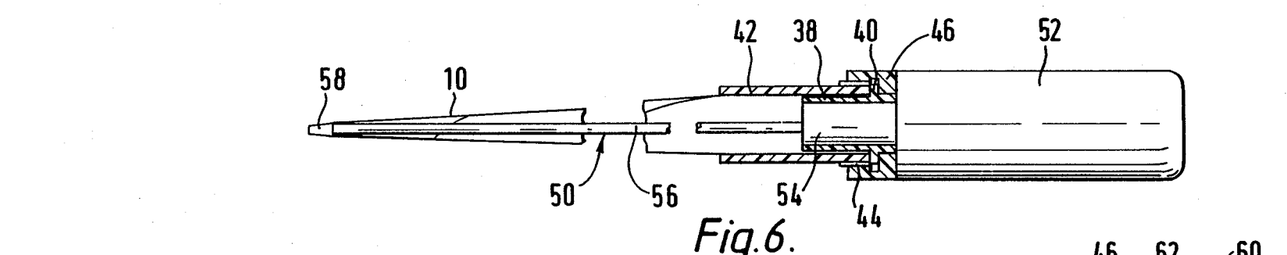
FIG. 6 is a longitudinal section through a completed cannula with a guide rod fitted.
Figure 7:
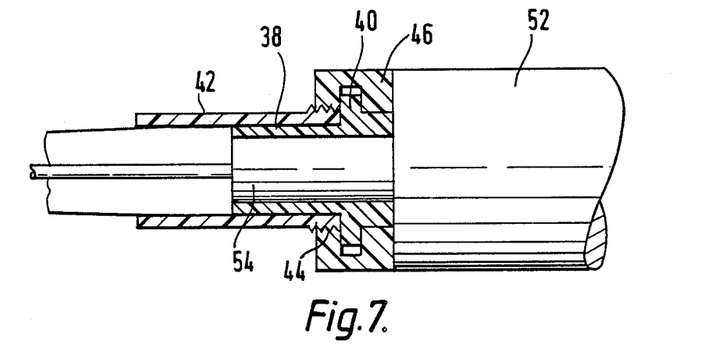
FIG. 7 is a detail of part of the cannula shown in FIG. 6 to a larger scale.

Referring now to FIG. 6, there is illustrated a guide rod 50, which comprises a handle 52; a boss 54 projecting from the handle and having an outside diameter such that it is a sliding fit in the bush 38; a rod-like stem 56 has a diameter of approximately 3 millimeters, and tapers slightly towards its distal end. The enlarged distal end 58 is conical, and its larger end has a diameter of about 3 millimeters. The rod-like stem 56 extends through the boss 54 of that handle 52, and the stem is bored throughout its length, to accept a wire.

Figure 8:
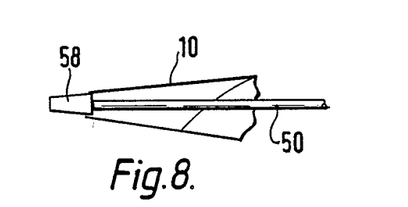
FIG. 8 is a detail of the distal end of the cannula during its expansion to receive a guide rod.
Figures 9, 14:
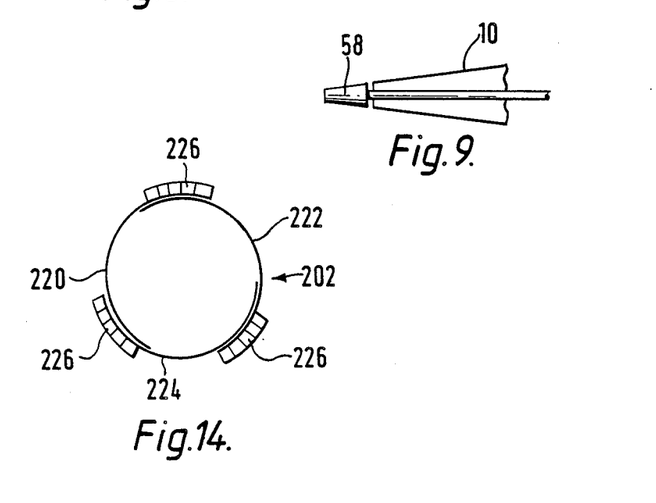
FIG. 9 is a view similar to FIG. 8, but showing the position at the end of fitting the guide rod.
FIG. 14 is an end view on the proximal end of a stem shown in FIG. 13.

When the guide rod 50 is to be used, its stem 56 is pushed through the bore of the conical cannula stem 10, and towards the end of this movement, the boss 54 slides in the bush 38 which serves to locate the stem 56 centrally within the stem 10. Near to the end of the forward movement of the guide rod, the enlarged head 58 passes out through the distal end of the stem 10. In doing so, it will slightly enlarge the distal end of the stem 10 (this being permitted by the resilience of that stem) as shown in FIG. 8, until the whole of the head 58 is outside the stem 10, whereupon the distal end of the stem 10 will contract behind the enlarged head 58 as shown in FIG. 9. At this stage, the handle 52 will be in engagement with the nut 46 as illustrated in FIG. 6. The stem 10 then provides a smooth continuation of the cone formed by the enlarged head 58 on the distal end of the guide rod 50, The complete cannula with the inserted guide rod 50 forms a trocar which is then ready for use.

Figures 10, 11:
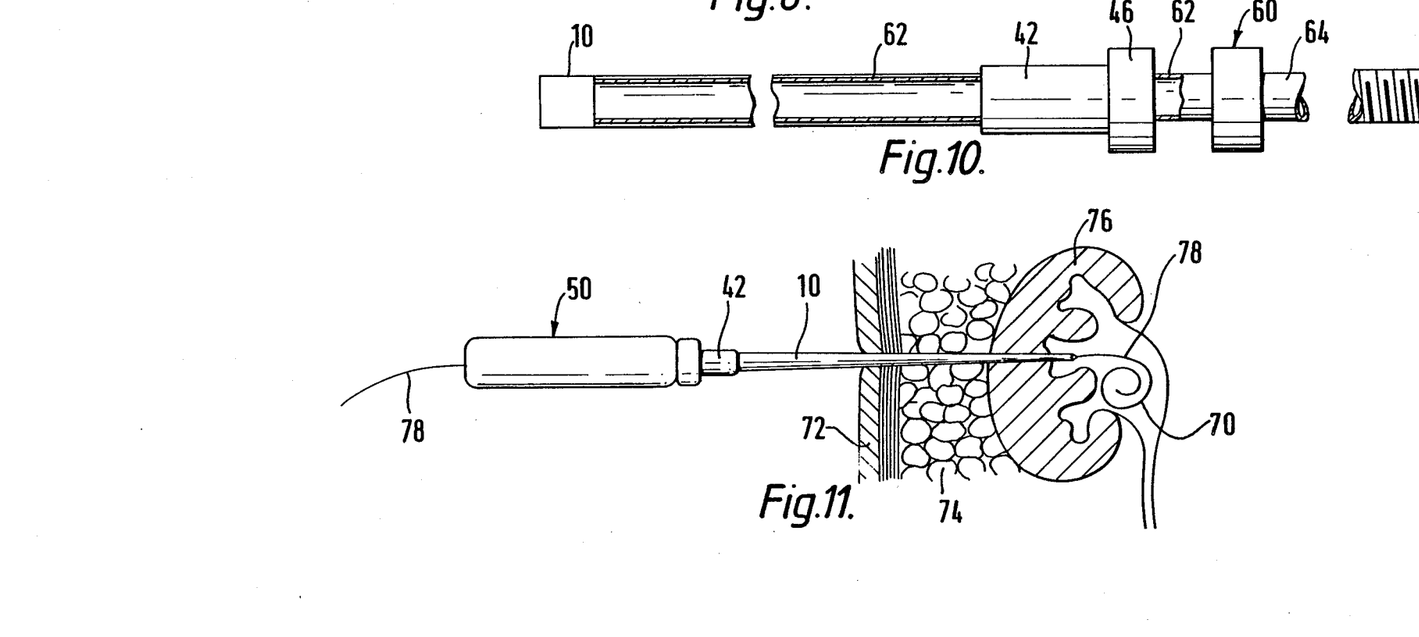
FIG. 10 is an elevation partly in section of the cannula stem shown in FIG. 6 during the insertion of a nephroscope.
FIG. 11 shows an initial stage in the use of the cannula in an operation to remove a stone from the renal pelvis of a kidney.
Figure 11:
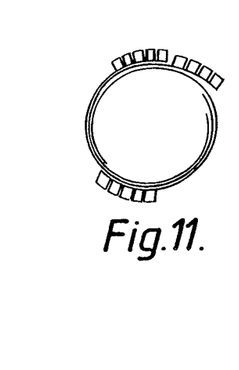

Turning to FIG. 10, there is illustrated a nephroscope 60 being used in conjunction with the cannula. Nephroscopes are in themselves known instruments, and essentially comprise a parallel-sided metal tube 62 with an extension which is adapted to receive an optical system and other items (not shown) whereby the surgeon is able to see through the tube 62, to the site of the lesion.

When the nephroscope 60 is to be used, the tubular portion 62 is introduced through the bush 38, in which it is a sliding fit, and then it is pushed forwardly relatively to the stem 10. It will be appreciated that the tubular member 42 and the nut 46 provide a means whereby the stem 10 can be held in one hand, whilst the nephroscope is gripped in the other hand. As the blunt front end of the tubular portion 63 of the nephroscope advances along the inside of the stem 10, it engages with the bore of that stem, and causes the stem to expand radially outwards, as permitted by uncoiling of the stem. Eventually, the position is arrived at as illustrated in FIG. 10, where the tubular portion 62 fully opens the coiled stem 10, so that for most of its length the latter then forms a substantially parallel-sided tube, closely embracing the outside of the tubular portion 62. In practice, when the nephroscope is fully positioned in the cannula, with a boss 61 engaged with the nut 46, the distal end of the nephroscope will project very slightly from the distal end of the stem. In this condition the instrument functions as a cannula rather than a trocar.

A method of using the apparatus so far described, during an operation for the removal of a kidney stone from the renal pelvis will now be described by way of example only of a use of the invention.

A fine needle, with a sharpened point (not shown) of a type used for the introduction of a guide wire through the tissue of a patient, is first passed through the skin 72 of the patent's loin (see FIG. 11), then through the fatty tissue 74 and into the renal pelvis under X-ray guidance. To ensure that the needle has reached the correct position, radio opaque dye may be injected down the needle and its dispersal into the renal pelvis viewed. A special guide wire 78 of the kind used for percutaneous surgery, and about 0.7 mm diameter is then threaded through the bore of the needle, until the front end of this wire arrives in the renal pelvis. The special wire 78 has a wire core around which is closely wound a fine wire covering. The core wire is pulled, to cause the front end of the wire to coil on itself as shown at 70 in FIG. 11, thereby locating and anchoring the front end of the wire in the renal pelvis. The needle itself is then withdrawn from the patient over the guide wire 78, leaving that wire in position. The method of inserting the guide wire which has been described so far is part of the known technique for the removal of a stone from the renal pelvis and no further description of this part of the operation is necessary.

At that stage, the guide rod 50 shown in FIG. 6, which has a somewhat larger diameter than the special needle through which the guide wire is inserted, is introduced into the cannula stem 10 until it occupies the fully inserted position illustrated in FIG. 6. It will be recalled that, in this position, the stem 10 of the trocar remains in the fully closed condition, and the tapering outside of the stem 10 forms in effect a continuation of the tapering enlarged end 58 of the guide rod 50.

The proximal end of the guide wire 78 is threaded through the guide rod 50 from the distal end thereof and out through the handle 52. The trocar comprising the stem 10 and the inserted guide rod 50, is then advanced along the guide wire 78, through the small incision in the skin 72 made by the special guide wire needle, through the fatty tissue 74, and into the renal pelvis. However, it will be appreciated, that because of the small cone angle of the stem 10 of the trocar, the dilation of the incision and openings through the patient's tissue brought about by the insertion of the trocar is facilitated, and will not normally result in any severe damage to the tissue, or severe internal haemorrhage.

At that point, the guide rod 50 is retracted from the trocar, drawing the guide rod 50 over the guide wire 78. This leaves the trocar stem in situ passing through the skin of the patient and into the renal pelvis.

The tubular portion 62 of the nephroscope 60 is then introduced through the bush 38 of the trocar, and the nephroscope is pushed inwardly. It will be appreciated, that the tubular portion 42 and the nut 46 provide an effecive handle for the trocar which can be gripped by the person performing the operation in one hand, whilst the extension 64 of the nephroscope can be gripped in the other hand. Moreover, the bush 38 provides guidance for the forward sliding motion of the tubular portion 62, to keep that portion centrally located within the stem 10 of the trocar.

As the tubular portion advances, it engages with the inside surface of the stem 10. During further advancing motion of the tubular portion 62, the stem 10 is caused to expand radially outwards, by uncoiling, until eventually, when the nephroscope is fully inserted the stem 10 forms a substantially parallel-sided tube closely embracing the tubular portion 62 of the nephroscope.

The radial expansion of the trocar stem is achieved in response to longitudinal motion of the tubular portion 62, and again, because of the small cone angle of the stem 10, the resulting dilation of the tissue is achieved with relatively small damage to the tissue, and certainly without any danger of cutting blood vessels.

Once the distal end of the nephroscope arrives in the renal pelvis, it is then possible to extract the stone via the nephroscope using known techniques, and at this stage the instrument is functioning as a cannula. Finally, the nephroscope and the expansible cannula are withdrawn together. If required, a nephrostomy tube may be passed down the nephroscope prior to its withdrawal, and the tube left in situ for drainage purposes.

After withdrawal of the expansible cannula, the tissue which has been compressed on dilation of the opening re-expands and swells, and since no tissue has been removed, the dilated passage through the tissue becomes occluded, thereby preventing excessive haemorrhage and allowing the tissue to recover with its structures intact.

Besides using the expansible cannula for introducing nephroscopes into the kidney, there are numerous other possible uses for the device. It will be understood, that the cannula may be made in any desired dimensions, according to the use to which it is intended to be put.

Some examples of possible alternative uses of the cannula—when appropriately modified—are:

(1) The insertion of pleuroscopes and mediastinoscopes into the chest for diagnosis, biopsy and other treatments.

(2) Insertion of chest drains for the treatment of pneumothorax of the drainage of pus.

(3) Insertion of laparoscopes into the abdomen for diagnosis, biopsy and other treatment.

(4) Insertion of drains into intra abdominal abcesses, cysts or fluid collections e.g. hepatic, sub diaphragmatic retropancreatic, perinephric and pelvic collections.

(5) Insertion of peritoneal dialysis catheters or nephrostomy tubes.

(6) Insertion of suprapubic cystascopes for the treatment of bladder tumours, prostatectomy and stone removal. (Suprapubic insertion of scopes into the bladder prevents trauma to, and subsequent stricture of the uretha. It also enables larger diameter scopes and intruments to be passed.) Suprapubic catheters may also be passed easily with the cannula.

(7) The expansible cannula may be used to pass a bone biopsy instrument through overlying tissues and into the bone surface.

(8) If the tip of the guide rod 50 within the cannula is blunt-ended, the device may be used as a dilator of bodily tubes or openings.

In the cannula described with references to FIGS. 1 to 11 of the drawings the expansible stem 10 is conical throughout its length. It is to be understood however that the stem may be conical through only part of its length, although if the stem is made as a single component the conical portion must be of substantial length in order to ensure that on the one hand a sufficient dilation effect is obtained using the one instrument and on the other hand that the cone angle is kept small—and preferably not more than 10°.

Further in the specific embodiment described above the nephroscope 60 is employed to expand the stem 10 of the cannula, but it is to be understood that any implement which is thick enough to cause opening of the coils of the stem could be inserted. In one respect therefore the invention comprises the combination of a cannula having the essential features of the cannula herein described with an opening device which can be pushed axially into the stem and will cause opening of the stem to increase its diameter.

Figure 12:
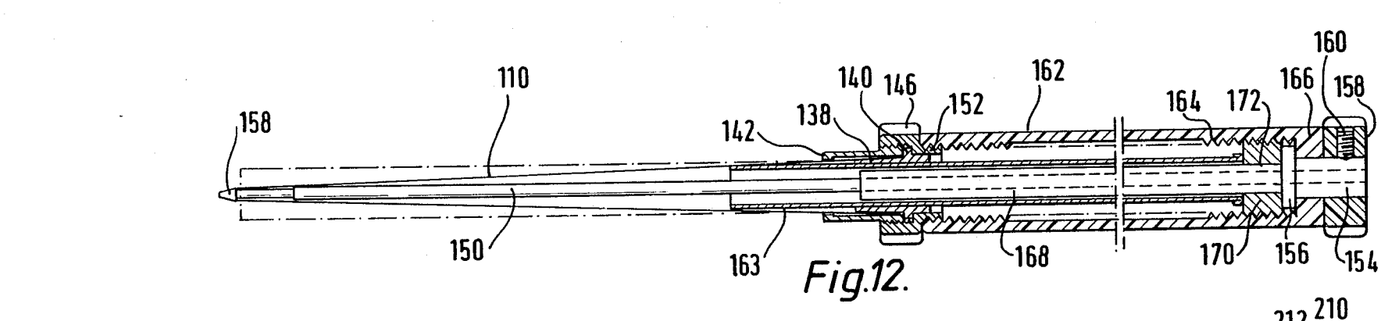
FIG. 12 is a longitudinal section through an alternative construction of cannula with a built-on opening mechanism.

Referring now to FIG. 12, there is illustrated a cannula, the expansible part of which is virtually identical with that described with reference to FIGS. 1 to 11. In particular, the cannula illustrated in FIG. 12 has an expansible conical stem 110, which is identical with that described with reference to FIGS. 1 to 5 of the drawings, and which at its proximal end is clamped between a collar 140 on a bush 138 and one end of a tube 142. Moreover, the tube 142 has an external screw thread, which is engaged by the internal screw thread of a retaining nut 146, which completes the joint between the bush 138 and the tube 142 nipping the flange formed at the proximal end of the stem 110 as described with reference to FIGS. 1 to 11.

There are some minor differences in the construction. For instance, the bore of the tube 142 is relieved, along most of its length, so that it only engages with the outside of the stem 110 near to the flange formed on the proximal end of the stem, and at the distal end of the tube 142 itself. Moreover, the arrangement is such, that even in the fully open position of the stem, which is illustrated in chain-dotted lines in FIG. 12, the stem is still very slightly tapered towards the distal end.

Another slight difference in the construction is that the retaining nut 146 is formed with a short extension 152, which is screw-threaded externally.

A finely bored guide rod 150 is provided, and this guide rod is in itself identical with the guide rod 50 illustrated in FIG. 6, and in particular, it has the frusto-conical distal end 158. However, the guide rod 150 is considerably longer than the guide rod 50, because as will hereinafter appear, the total length of the cannula through which the guide rod has to pass is appreciably longer than that illustrated in FIG. 6.

A cylindrical sleeve 162 made of transparent or translucent plastics material is provided as part of a mechanism for the introduction of an expander tube 163, and the length of the sleeve 162 is determined by the length of movement of the expander tube necessary to cause movement of the stem 110 from the fully closed to the fully open condition as described with reference to the construction illustrated in FIGS. 1 to 11.

Internally, the sleeve 162 is screw-threaded at 164 throughout practically the whole of its length, and at its distal end, the sleeve is open, and the screw thread 164 can be engaged on the screw-threaded extension 152 of the retaining nut 146. Thus, the sleeve 162 can be assembled on to the nut 146, and in this assembled condition, it provides part of the complete cannula.

As illustrated in FIG. 12, the proximal end of the sleeve 162 is partially closed by an end cap 166, but this end cap is bored to receive a boss 154 formed on the proximal end of a longitudinally extending actuation member 168. The main section of the actuation member 168 is of square cross-section, and there is a collar 156 between the boss 154 and the square cross-section main portion of the actuation member. As illustrated in FIG. 12, when the apparatus is assembled, the collar 156 engages with the inside face of the end cap 166. On the outwardly projecting portion of the boss 54 there is a finger grip device 158, which is secured by a grub screw 160.

A traversing nut 170 is screw-threaded externally to engage in the internal screw threads 164 in the sleeve 162, and internally is formed with a square bore 172 which is a sliding fit on the main portion of the actuation member 168. Now if the finger grip 158 is turned by hand, this turns the actuation member 168, and because of the square cross-section of the actuation member and the bore of the actuation nut, the latter is also turned. Turning the nut 170 causes it to travel along the inside of the sleeve 162 because of its screw-threaded engagement with that sleeve, but the actuation member 168 cannot move longitudinally (since the end cap 166 is located between the finger grip member 158 and the collar 156) and therefore the actuation nut 170 slides on the main portion of the actuation member 168. This therefore provides a means whereby the nut 170 can be caused to travel longitudinally along the inside of the sleeve 162 by rotation of the finger grip member 158. It will be appreciated however, that there is a considerable mechanical advantage provided by the screw method of operation, so that an appreciable force can be applied through the nut 170 by turning the finger grip member 158.

The expander tube 163 is threaded through the bore of the bush 138, and is a clearance fit around the outside of the actuation member 168. Its proximal end is pressed into engagement with the nut 170.

To operate the cannula, after the guide rod 150 has been inserted through the bore of the actuation member 168 and through the stem 110, rotation of the actuation member causes the nut 170 to travel towards the distal end of the sleeve 162, and in so doing, it pushes the exapnder tube 163 towards the distal end of the stem 110, expanding the stem until it reaches the fully open condition illustrated in chain-dotted lines in FIG. 12.

It will be appreciated therefore, that the cannula illustrated in FIG. 12 operates in generally the same manner as that described with reference to FIGS. 1 to 11, except for the provision of the screw-and-nut method of forcing the nephroscope through the expansible stem of the cannula.

After the expander tube 163 has been fully inserted, the sleeve 166 is unscrewed from the retaining nut 146 and withdrawn. This provides easy access to the proximal end of the tube 163 for the insertion of a nephroscope or other instrument. One of the advantages of the construction shown in FIG. 12 is that it allows the guide wire to be left in situ whilst the expander tube is fitted and even after the expander tube and any instrument fitted in it is withdrawn. The facility for leaving the wire in situ arises from the fact, that the wire passes through the bore of the actuation member 168, and the fact that manual pressure is not applied to the end of the expander tube.

Figure 13:
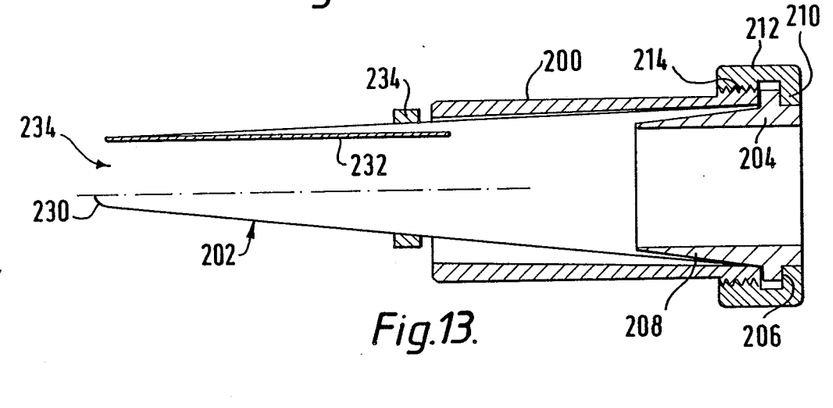
FIG. 13 is a longitudinal section through an alternative construction of cannula particularly useful in brain surgery, the bottom half of the view showing the closed condition and the top half the fully open condition.

The third embodiment of the invention is shown in FIGS. 13 and 14, and the apparatus illustrated provides a cannula which is particularly useful in brain surgery, for example in the removal of tumours from the brain. The essential features of this apparatus are a mounting tube 200 and an expansible stem 202.

The mounting tube 200 is a substantial metal tube (for instance it may have an outside diameter of 45 millimeters) and it is designed to be mounted on a support ring (not shown) of known construction, which is clamped to the scull of a patient to provide location for various investigatory and surgical items. A bush 204 has a portion 208 which is frusto-conical, and a collar 206 which is nipped between the proximal end of the mounting tube 200 and a shoulder 210 in a retaining nut 212 which engages on a screw thread 214 formed on the tube 200. The arrangement of the bush 204 within the tube 200 is very similar to the arrangement of the bush 38 in the tube 42 as previously described.

The stem 202 is however formed from three separate metal foil leaves 220, 222 and 224 (see FIG. 14). Each of the leaves 220, 222 and 224 is formed in beryllium copper and the method of formation to produce a seam along one edge, a doubled over reinforced portion, and a serrated double tab 226 are similar to that described with reference to FIGS. 1 to 5. Also the leaves are coiled and heat treated to give the spring effect. However, the leaves are relatively short—in a specific example approximately 160 millimeters long. The three leaves 220, 222 and 224 are assembled as shown in FIG. 14, so that each subtends more than 120° around the longitudinal axis of the stem even at the large proximal end, and each leaf has its tapering, seamed, edge inside the reinforced part of the leaf which is adjacent to it in the anticlockwise direction as seen in FIG. 14. Thus, each leaf engages over one adjacent leaf and under another adjacent leaf and together they subtend a full circle. The three tabs 226 are trapped between the tube 200 and the collar 206 on the bush 204 in similar manner to the tab on the single leaf stem shown in FIGS. 1 to 11, and in the free condition, the distal ends of the leaves close to a small diameter shown at 230 in FIG. 13—in fact, the distal ends are preferably turned inwards as shown at 230 to form a bull nose on the stem 202.

When apparatus illustrated in FIGS. 13 and 14 is in use, it is of course supported by being attached to the support ring, and it is therefore held quite rigidly. The stem 202, which will be in the closed condition illustrated in the lower half of FIG. 13, is pointed directly at the seat of the operation, and the distal end is introduced through an aperture previously made in the scull. At that stage, it is necessary to expand the stem 202, and for this purpose an expansion tube 232, only part of which is illustrated in FIG. 13, is introduced by sliding it through the bore of the bush 204. As the expansion tube 232 moves towards the distal end of the stem 202, it engages with the inside faces of the three leaves of the stem, and expansion is carried out, by causing the leaves to slide over each other into the fully opened condition, where they form a conical tube having a much smaller cone angle than that in the closed condition, so that a relatively large diameter opening 234 is formed at the distal end of the tube. In a specific embodiment, the opening may be 30 millimeters in diameter. This is adequate to allow instruments to be passed through the bore of the expansion tube 232 to the seat of the operation, and the expanded stem 202 holds the surrounding tissue away from the seat of the operation.

When the operation is completed, the expansion tube 232 is retracted, and this allows the stem 202 to contract into the closed condition. The opening and closing action of the three leaves of the stem 202 in some ways resembles the opening and closing action of a set of petals of a flower, although besides the radially outward motion, there is also an element of circumferential motion which increases towards the distal end of the stem.

A rubber ring 234 is a tight fit around the stem 202 adjacent to the distal end of the support tube 200. This ring assists in maintaining the circular configuration of the stem when the latter is fully opened.

It is to be understood, that various alternatives are possible. For instance, the stem 202 could comprise only two foil-like leaves, or in some instances, it could comprise more than three leaves.

The specification of United Kingdom Patent Application No. 8513702 from which this patent application claims priority uses the word "trocar" throughout to describe the apparatus provided by the invention. Although, in some of its uses, the instrument is performing as a trocar, that is an instrument for forming an opening through the skin and tissue, the word "cannula" is more descriptive of the instrument and has been used in this specification excepting where the instrument is being used to perform the function of a trocar.

What is claimed is:

1. An expansible cannula capable of piercing kidney or brain tissue comprising a conical stem having a proximal end and a distal end and means for securing the proximal end of the conical stem against opening, the conical stem being hollow with inner and outer walls and being formed of flexible resilient sheet material coiled on itself and biased by the resilience of the sheet material into a normally closed condition with the apex of the cone at the distal end of the stem, the larger, proximal end of the stem being larger in diameter than the distal end by a multiple greater than unity so that the coil subtends at least 360° about the longitudinal axis of the stem, and a rigid tubular member, for insertion into the stem through the proximal end, wherein the inner wall of the stem has a receiving surface which, when acted upon by the tubular member sliding along the length of the stem causes the stem to open from said normally closed conical angle whereby the stem becomes substantially cylindrical thereby increasing the diameter of the stem at the distal end to approximately the same as that at the proximal end while maintaining a closed circular diameter at all positions along its length, and the resilience of the stem being such that when the tube is withdrawn, the stem will contract back to its closed conical condition.

2. An expansible cannula according to claim 1, wherein said stem is made in sheet metal which is heat treated after coiling, to give it the required resilience.

3. An expansible cannula according to claim 2, wherein said stem is made in beryllium copper.

4. An expansible cannula according to any one of claims 1, 2 and 3, further comprising first and second tubular elements, said second tubular element being located inside the proximal end of said coiled stem and within said first tubular element, a proximal end of said stem being clamped between said first and second tubular elements, and means securing said first and second tubular elements together to effect clamping of said stem.

5. An expansible cannula according to claim 4, wherein said second tubular element has a collar engaging with the outer face of a flange on the end of said stem and said first tubular element engages with the opposite face of said flange, said means for securing said first and second tubular elements together comprising a nut engaging with the outer end of said collar, and having screw-threaded engagement with said first tubular element.

6. An expansible cannula according to any one of claims 1, 2 or 3, wherein the bore of said stem, at its distal end, in the closed condition, is a close fit around a guide rod, bored throughout its length, to pass over a wire extending through the skin of a patient to the site of the lesion.

7. An expansible cannula according to any one of claims 1, 2 or 3, wherein the cone angle of said stem does not exceed 10°.

8. An expansible cannula according to any one of claims 1, 2 or 3, further combined with a guide rod adapted to pass through the bore of said stem at its distal end, said guide rod being bored throughout its length to receive a guide wire, said guide rod being further formed with a slightly enlarged distal end, the arrangement of said stem providing that passage of such enlarged distal end through the distal end of said stem causes a slight opening out (uncoiling) of the distal end of said stem to allow passage of said enlargement, the distal end of said stem then contracting under its inherent resilience, on to said guide rod behind said enlarged end, so that said enlarged end is located against the distal end of said stem.

9. An expansible cannula according to claim 1, wherein said stem is formed by a plurality of thin sheet material leaves, each of arcuate cross-section, each said leaf being overlapped with the adjacent leaf or leaves so that, together said leaves form a tube which can be increased in diameter by moving said leaves to reduce the overlap between them.

10. An expansible cannula according to claim 9, wherein each said leaf has one longitudinal margin on the inside of an adjacent leaf and the other longitudinal margin on the outside of the or another leaf.

11. An expansible cannula according to claim 10, wherein said leaves taper so that in the assembled condition they form a conical or frusto-conical stem, which tapers towards the distal end, so that when said stem is opened by exerting an expansion force to the inside of said stem, the distal ends of said leaves open to a greater extent than the proximal end.

* * * * *